(12) United States Patent
Cutler et al.

(10) Patent No.: US 6,562,838 B2
(45) Date of Patent: May 13, 2003

(54) TREATMENT OF CARDIOVASCULAR DISEASE WITH QUINOLINONE ENANTIOMERS

(75) Inventors: Neal R. Cutler, Los Angeles, CA (US); John Sramek, Irvine, CA (US)

(73) Assignee: R. T. Alamo Ventures I, L.L.C., Beverly Hills, CA (US)

( * ) Notice: Subject to any disclaimer, the term of this patent is extended or adjusted under 35 U.S.C. 154(b) by 0 days.

(21) Appl. No.: 09/771,104

(22) Filed: Jan. 26, 2001

(65) Prior Publication Data

US 2002/0143031 A1 Oct. 3, 2002

(51) Int. Cl.[7] ............................................. A61K 31/47
(52) U.S. Cl. ...................................................... 514/312
(58) Field of Search ........................................ 514/312

(56) References Cited

U.S. PATENT DOCUMENTS

| | | | |
|---|---|---|---|
| 4,302,460 A | 11/1981 | Davies et al. | 424/258 |
| 4,311,707 A | 1/1982 | Birnbaum et al. | 424/305 |
| 4,522,884 A | 6/1985 | Brody | 428/400 |
| 4,552,891 A | 11/1985 | Ho et al. | 514/443 |
| 4,623,650 A | 11/1986 | Gilligan et al. | 514/312 |
| 4,710,506 A | 12/1987 | Davies et al. | 514/301 |
| 4,772,614 A | 9/1988 | Davies et al. | 514/312 |
| 4,855,291 A | 8/1989 | Davies | 514/312 |
| 4,877,793 A | 10/1989 | Davies | 514/301 |
| 4,997,840 A | 3/1991 | Davies et al. | 514/312 |
| 5,011,931 A | 4/1991 | MacLean et al. | 546/155 |
| 5,079,264 A | 1/1992 | MacLean et al. | 514/629 |
| 5,393,773 A | 2/1995 | Craig et al. | 514/415 |
| 5,554,639 A | 9/1996 | Craig et al. | 514/415 |
| 5,721,238 A | 2/1998 | Heiker et al. | 514/259 |
| 5,801,161 A | 9/1998 | Merkus | 514/52 |
| 5,864,037 A | 1/1999 | Chasin et al. | 544/118 |
| 5,869,479 A | 2/1999 | Kreutner et al. | 514/212 |
| 6,110,489 A | 8/2000 | Cutler | 424/449 |
| 6,132,753 A | 10/2000 | Cutler | 424/423 |
| 6,132,757 A | 10/2000 | Cutler | 424/434 |
| 6,187,790 B1 | 2/2001 | Cutler | 514/312 |
| 6,194,433 B1 | 2/2001 | Cutler | 514/312 |

FOREIGN PATENT DOCUMENTS

| WO | WO 94/02144 | 2/1994 |
|---|---|---|
| WO | WO 00/07595 | 2/2000 |

OTHER PUBLICATIONS

Morita et al., Chem. Pharm. Bull., 42(10), 2157–60 (1994).*
Kashiyama et al., Xenobiotica, 24(4), 369–77 (Apr., 1994).*
McMurry, *Organic Chemistry*, 2nd Ed., Brooks/Cole Publishing, Belmont, CA (1988), pp. 1044–1045 and 1076.
Kelso et al., "Actions of the Novel Vasodilator, Flosequinan, in Isolated Ventricular Cardiomyocytes," *J. Cardiovasc. Pharmacol.* 25:376–386 (1995).

Perreault et al., "Differential inotropic effects of flosequinan in ventricular muscle from noemal ferrets versus patients with end–stage heart failure," *Br. J. Pharmacol.* 106:511–516 (1992).
Jones et al., "Effect of flosequinan on ischaemia–induced arrhythmias and on ventricular cyclic nucleotide content in the anaestetized rat," *Br. J. Pharmacol.* 108:1111–1116 (1993).
Gristwood et al., "Studies on the cardiac actions of flosequinan in vitro," *Br. J. Pharmacol.* 105:985–991 (1992).
Frodsham et al., "Effect of flosequinan upon isoenzymes of phosphodiesterase from guinea–pig cardiac and vascular smooth muscle," *Eur. J. Pharmacol.* 211:383–391 (1992).
Medical Sciences Bulletin, "Do We Need More Antihypertensive Agents?" No. 238; p. 1 (1997).
Gaafar K., et al.,Studies on the Glycemic and Lipidemic Effect of Atenolol and Propranolol in Normal and Diabetic Rats, *Arzneimittelforschung*, 44(4): 496–501 (Apr., 1994) (Abstract Only).
Shiraishi et al., "Effect of cilostazol, a phosphodiesterase type III inhibitor, on histamine–induced increase in $[Ca^{2+}]i$ and force in middle cerebral artery of the rabbit," *Br. J. Pharmacol.*, 123: 869–878 (1998).
Medical Sciences Bulletin, "Flosequinan for Congestive Heart Failure" (Mar., 1993).
Kashiyama et al., "Cytochrome P450 responsible for the Stereoselective S–oxidation of Flosequinan in Hepatic Microsomes from Rats and Humans," *Drug Metab and Disp.* 25(6). 716 (1997).
Uno et al., "Synthesis of 2(1H)–Quinolinone Derivatives and Their Inhibitory Activity on the Release of 12(S)–Hydroxyeicosatetraenoic (12–HETE) from Platelets" *Chem Pharm Bull* 43(10):1724–1733 (1995).
Kaufmann et al. "Characterization and Pharmacological Relevance of High Affinity Binding Sites for [3H] LY186126, a Cardiotonic Phosphodiesterase Inhibitor, in Canine Cardiac Membranes" *Circulation Research* 65:154 (1989).
Silver et al. "Differential pharmacologic sensitivity of cyclic nucleotide phosphodiesterase isozymes isolated from cardiac muscle, arterial and airway smooth muscle" *Eur J Pharmacol* 150:85 (1988).
Ikezono et al. "General Pharmacological Properties of the New Vasodilator Flosequinan" *Arzheim–Forsch/ Drug Res* 42 (II) (10):1200–1211 (1992).

\* cited by examiner

*Primary Examiner*—Phyllis G. Spivack
(74) *Attorney, Agent, or Firm*—Medlen & Carroll, LLP

(57) ABSTRACT

The present invention is directed to methods for treating cardiovascular disease comprising administering the enantiomers of flosequinan in subjects not concurrently treated with nitrites or nitrates.

8 Claims, 2 Drawing Sheets

TREATMENT OF CARDIOVASCULAR DISEASE WITH QUINOLINONE ENANTIOMERS

FIELD OF THE INVENTION

The present invention relates to compositions and methods for the treatment of cardiovascular disease.

BACKGROUND

Cardiovascular disease is the number one cause of death in the United States. Medical Sciences Bulletin, No. 238; p. 1 (1997). While cardiovascular disease presents many different clinical manifestations, hypertension and congestive heart failure (CHF) are major components of this disease state. Uncontrolled hypertension can result in myocardial infarction and stroke. Congestive heart failure, if untreated, is an ultimately fatal disease that kills more than half its victims within five years of initial diagnosis. CHF affects about 3 million people in the United States and about 15 million worldwide. Currently, an estimated 400,000 new cases are diagnosed in the United States each year, and CHF is responsible for about 900,000 hospitalizations a year.

The current treatment approaches involve anti-hypertensive compounds, such as: beta-blockers, calcium channel blockers (especially dihydropyrimidines), angiotensin-converting enzyme (ACE) inhibitors, diuretics, and alpha-blockers. However, many patients fail to respond to (or tolerate poorly) these compounds.

For example, many patients do not respond to diuretics (with or without digitalis). Moreover, many patients cannot tolerate (or respond poorly to) ACE inhibitors. In addition the use of beta blockers has been associated with loss of glycemic control. Studies on the Glycemic and Lipidemic Effect of Atenolol and Propranolol in Normal and Diabetic Rats, (Abstract), Arzneimittelforschung, 44(4): 496–501 (April, 1994).

What is needed, therefore, is an pharmacological intervention for cardiovascular disease (including, but limited to, hypertension and CHF) that is less disruptive to the patient and is be better tolerated in comparison to existing treatment modalities.

SUMMARY OF THE INVENTION

The present invention provides compositions and methods for the treatment of cardiovascular disease. In a preferred embodiment, the present invention is particularly suited to the treatment of CHF. The methods of the present invention comprise the administration of pharmaceutical compositions to subjects who, in a preferred embodiment, are not concurrently administered nitrites and nitrates. Specifically, the compositions of the present invention comprise quinolinones, including derivatives thereof. Quinolinones are also known as quinolones and oxoquinolines.

In another embodiment, the present invention contemplates halogenated quinolinones (e.g., fluoroquinolinone). In a preferred embodiment, the quinolinone is a thioquinolinone or a sulphinyl or suphonyl derivatives thereof. In one embodiment, the halogenated quinolinone is flosequinan [(+−)-7-fluoro-1-methyl-3-(methyl-sulphinyl)-4(1H)-quinolinone]; [7-Fluoro-1-methyl-3-(methylsufinyl)-4(1H)-quinolone]. In a preferred embodiment, an enantiomer [either (+) or (−)] of flosequinan is used.

In one embodiment, the present invention contemplates a method, comprising: a) providing: i) a patient presenting at least one symptom of cardiovascular disease, and ii) a purified enantiomer preparation of flosequinan; and b) administering said preparation to said patient (e.g. such that said symptom is reduced). A variety of such symptoms of cardiovascular disease are contemplated. It is not intended that the present invention be limited to the reduction of a particular symptom of cardiovascular disease. In a preferred embodiment, the a symptom of hypertension is reduced.

Hypertension is an abnormal increase of blood pressure in the arteries continuing over a period of time. It occurs when the arterioles, the small blood vessels that branch off from the arteries, become constricted. This constriction of the arterioles makes it difficult for blood to flow which increases pressure against the artery walls.

A blood pressure reading of approximately $^{110}/_{60}$ to $^{140}/_{60}$ is considered to be in the normal range. The first number (110) is the systolic pressure which measures the blood pressure in the arteries when the heart is contracting and pumping blood. The second number (60) is the diastolic pressure which measures the blood pressure in the arteries when the heart is at rest. Hypertension adds to the workload of the heart and arteries. Over time, this can lead to heart and blood vessel damage which causes hardening of the arteries, heart failure, stroke, kidneys problems, blindness, and brain damage. In one embodiment of the present invention, a symptom of cardiovascular disease comprises a measured blood pressure of approximately $^{140}/_{60}$ or higher. In a preferred embodiment, the diagnosis of said hypertensive blood pressure (e.g. approximately $^{140}/_{60}$ or higher) is confirmed by a plurality of measurements of approximately $^{140}/_{60}$ or higher spaced over the period of at least two weeks. It is not intended that the present invention be limited by the means by which blood pressure is measured. Moreover, additional symptoms of hypertension also include, but are not limited to, tiredness, confusion, nausea, vomiting, anxiety, excessive perspiration, muscle tremor, chest pain, nosebleed, and buzzing in the ears.

In another embodiment, the present invention contemplates compositions and methods to reduce the symptoms of CHF (also referred to as 'heart failure'). CHF is characterized by an inadequacy of the heart so that, as a pump, it fails to maintain the circulation of blood, such that congestion and edema develop in the tissues of the heart are reduced. Symptoms of CHF include, but are not limited to, shortness of breath, pitting edema, an enlarged and tender liver, engorged neck veins, and pulmonary rates in various combinations.

It is not intended that the present invention be limited by the method by which CHF is diagnosed. CHF may be diagnosed based on a medical history and complete physical examination, which may include a blood pressure check, listening to the subject's heart through a stethoscope and taking the subject's pulse. At physical exam a Health Care Provider (including, but not limited to, Physicians, Nurse Practitioners, or Physician's Assistants) may look for the symptoms of CHF (as listed above).

If a Health Care Provider does not find enough symptoms to make a diagnosis, but is still suspicious that the subject has CHF, then her or she may order further tests. These test include, but are not limited to, blood tests to assess for anemia and thyroid function, urine tests to measure sugar, an Electrocardiogram (EKG), an exercise stress test, an Echocardiogram, a stress echocardiogram, radionuclide imaging tests (such as a radionuclide ventriculogram).

More invasive exploratory tests may also be ordered in conjunction with, or instead of the above. These tests include a coronary angiogram, in which a contrast dye is delivered by catheter to the coronary arteries to visualize the blood vessels and identify heart damage or dysfunction.

The present invention is not limited by the degree of response by the subject. It is expected that the administration of quinolinone enantiomers will reduce the symptoms associated with cardiovascular diseases including, but not limited to, angina pectoris, myocardial infarction, congestive heart failure, cardiomyopathy, hypertension, arterial stenosis, and venous stenosis. In a preferred embodiment, the enantiomers of flosequinan are administered to reduce the symptoms associated with hypertension.

In another preferred embodiment, the enantiomers of flosequinan are administered to reduce the symptoms of CHF. The symptoms of CHF include, but are not limited to, shortness of breath, pitting edema, an enlarged and tender liver, engorged neck veins, and pulmonary rates in various combinations.

Symptoms are "reduced" when the magnitude (e.g. intensity) or frequency of symptoms is reduced. It is not intended that the present invention be limited only to cases where the symptoms are eliminated. The present invention specifically contemplates treatment such that symptoms are reduced (and the condition of the subject is thereby "improved"), albeit not completely eliminated.

In a preferred embodiment, the subject is a human and the oral dosage of either the (+) or (−) enantiomer of flosequinan is in a single dose per day of up to approximately two hundred milligrams. In another embodiment said dosage is between approximately twenty-five to approximately seventy-five milligrams. In another embodiment, the (+) or the (−) enantiomer is administered in a single oral dose per day of between approximately one hundred and twenty-five and approximately two hundred milligrams. In another embodiment, the administration of said enantiomers of flosequinan comprises three daily doses, before meals, each dose of up to approximately two hundred milligrams per dose. In another embodiment, said daily doses comprise between approximately twenty-five to approximately seventy-five milligrams per dose. In another embodiment, said daily doses comprise between approximately one hundred and twenty-five and approximately two hundred milligrams per dose.

In selected embodiments said enantiomers of flosequinan are introduced orally, cutaneously, by standard injection (e.g. intravenously), or intranasally.

In one embodiment, the method comprises a) providing: i) a patient suffering from symptoms of cardiac disease who is not being administered nitrates or nitrites; and ii) an enantiomer of flosequinan; and b) introducing said enantiomer of flosequinan to said patient such that said symptoms of cardiac disease are reduced.

In one embodiment, said substantially purified enantiomer of flosequinan is a (+) enantiomer. In another embodiment, said composition is substantially free of the (−) enantiomer of flosequinan.

In one embodiment, the method comprises a) providing: i) a subject suffering from symptoms of cardiovascular disease; and ii) a purified enantiomer preparation of flosequinan, or a pharmaceutically acceptable salt thereof; and b) administering said preparation to the subject such that symptoms are reduced. In one embodiment, said cardiovascular disease is selected from the group consisting of hypertension, angina pectoris, myocardial infarction, and congestive heart failure. Said administering step is selected from the routes consisting of intranasal and respiratory inhalation.

In another embodiment, the method comprises a) providing: i) a subject suffering from symptoms of cardiovascular disease who is not being treated with a drug that causes hypotensive effects, and ii) a purified enantiomer preparation of flosequinan, or a pharmaceutically acceptable salt thereof; and b) administering said preparation to the subject such that such symptoms are reduced.

In another embodiment, the method comprises a) providing: i) a subject suffering from symptoms of cardiovascular disease who is not being treated with a nitrite or nitrate, and ii) a purified enantiomer preparation of flosequinan, or a pharmaceutically acceptable salt thereof; and b) introducing said preparation to the subject such that such symptoms are reduced. Said nitrate is selected from the group consisting of glyceryl trinitrate, isosorbide dinitrate, isosorbide-5'-mononitrate, and erythrityl tetranitrate.

It is not intended that the present invention be limited by the method of introduction of a purified enantiomer preparation of flosequinan, or a pharmaceutically acceptable salt thereof. In one embodiment, the enantiomer of flosequinan is introduced orally. In a preferred embodiment, an adult human is provided an oral dosage as a single dose per day of 10 to 200 milligrams. In other embodiments, enantiomers of flosequinan are introduced cutaneously, by standard injection, intranasally, or through respiratory inhalation.

The present invention is not limited by the degree of response by the subject. In one embodiment, relief of pain from angina pectoris is sufficient.

It is not intended that the present invention be limited by the nature of the formulation. In one embodiment, the present invention contemplates a mixture of a purified enantiomer of flosequinan and a carrier, i.e. a mixture comprising lactose.

In one embodiment, the enantiomers recited in the present invention are introduced into said subject by oral administration or cutaneous administration. In another embodiment, said subject is an adult human and said oral administration comprises up to approximately 200 milligrams of flosequinan.

In a preferred embodiment, the enantiomers of flosequinan recited in the present invention are administered to a subject who has not been treated in the past with a drug that causes hypotensive effects. In a more preferred embodiment, the enantiomers of flosequinan recited in the present invention are administered to a subject who is not being treated with a nitrite or nitrate. In one embodiment said nitrate is selected from the group consisting of glyceryl trinitrate, isosorbide dinitrate, isosorbide-5-mononitrate and erythrityl tetranitrate.

The present invention also contemplates a method, comprising: a) providing: i) a subject suffering from a symptom of a cardiovascular disease selected from the group of hypertension and congestive heart failure and; ii) a purified enantiomer preparation of flosequinan and; b) administering said preparation to said subject under conditions such that said symptom is reduced. In a preferred embodiment, said purified enantiomer of flosequinan is the (+) enantiomer. In another preferred embodiment, said purified enantiomer of flosequinan is the (−) enantiomer.

In one embodiment, the enantiomer preparation introduced into said subject by oral or cutaneous administration. In one embodiment said subject is an adult human and said oral administration, of said enantiomer preparation, comprises up to approximately 200 milligrams of flosequinan.

The present invention also contemplates a purified flosequinan enantiomer preparation comprising a carrier.

DEFINITIONS

Figure 1:
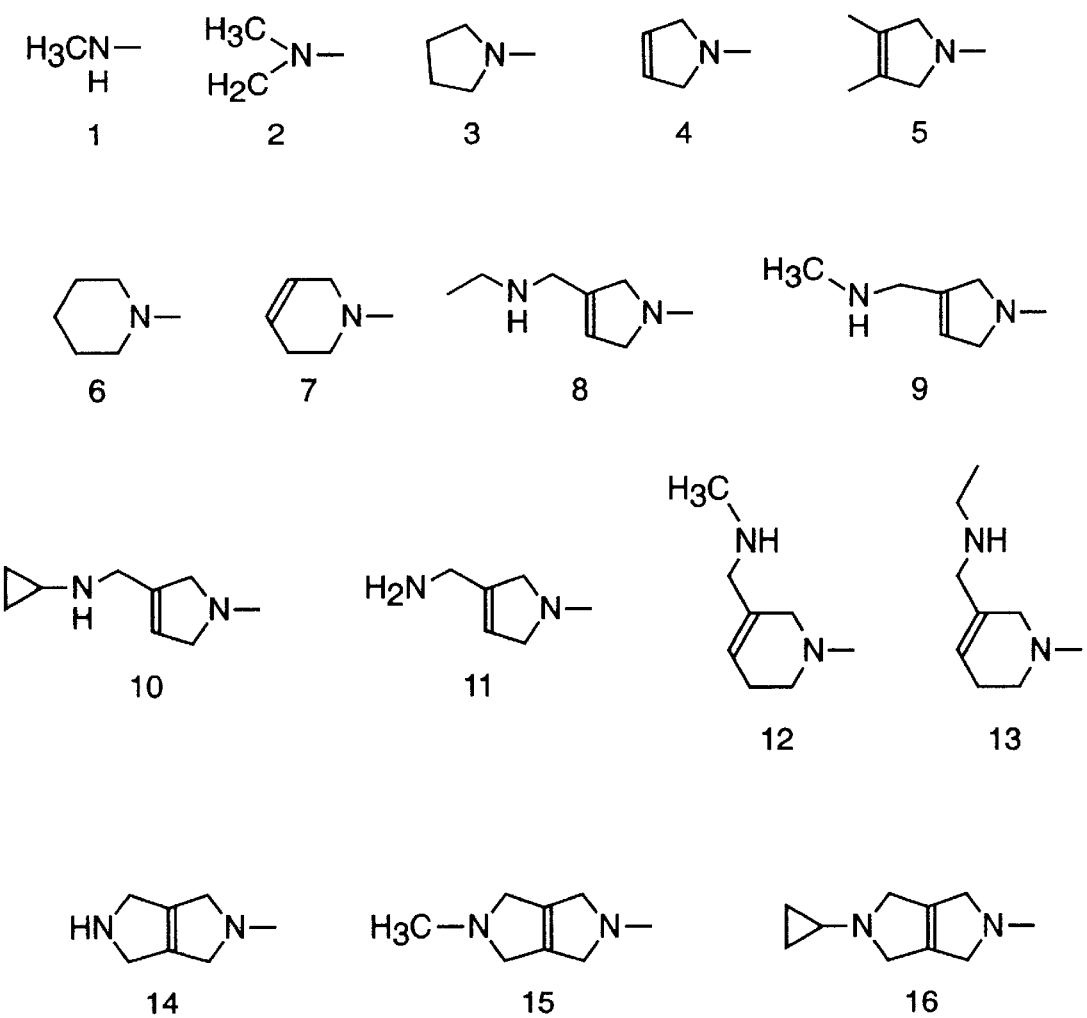
FIG. 1 depicts the chemical structure of a quinolinone (top) and 16 C-7 substituents (bottom).

As used herein, the term "quinolinone" refers to chemical compositions comprising quinolinone as set forth in the following structure (2-quinolone):

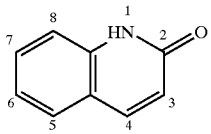

as well as other forms of quinolinone, (e.g., isoquinolone):

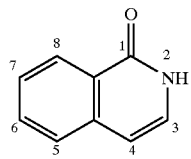

As used herein, the phrase "derivatives of quinolinone" refers to chemical compositions comprising quinolinone with a chemical group attached, including (but not limited to) halogenated quinolinones.

As used herein, the phrase "methylsulphinyl derivatives of quinolinone" refers to chemical compositions comprising quinolinone with a methylsulphinyl group attached. Examples include flosequinan (7-fluoro-1-methyl-3-(methylsulphinyl)-4(1H)-quinolone; 7-fluoro-1-methyl-3-(methylsufinyl)-4(1H)-quinolinone):

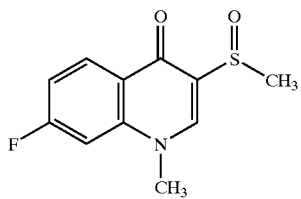

and sulfone metabolites of flosequinan:

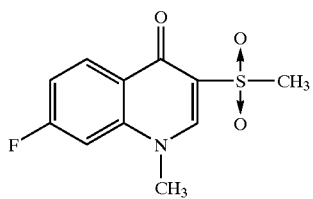

As used herein, "drugs that have hypotensive effects" are those drugs which, when administered, cause the subject's end-diastolic blood pressure to be reduced. Nitrates are commonly used drugs which have hypotensive effects.

As used herein, "nitrates" are compounds that contain the $-NO_3-$ moiety. Nitrates typically used in the clinic are shown in Table 1.

As used herein, "nitrites" are compounds that contain the $-NO_2-$ moiety. Nitrites typically used in the clinic are shown in Table 1.

As used herein "standard injection" refers to the placement of a pharmaceutical composition into a subject (e.g., with a hypodermic needle). For example, such injection can be made subcutaneously, intravenously, intramuscularly, intracavernosally, etc.

As used herein, "by oral administration" refers to the introduction of a pharmaceutical composition into a subject by way of the oral cavity (e.g., in aqueous liquid or solid form).

As used herein, the term "subject" refers to both humans and animals.

As used herein, "cutaneously" refers to the introduction of a pharmaceutical composition into a subject by application to the surface of the skin such that the composition is absorbed into the subject.

As used herein, "intranasally" refers to the introduction of a pharmaceutical composition within the nasal cavity.

As used herein, "respiratory inhalation" refers to the introduction of a pharmaceutical composition within the respiratory tract.

As used herein "single dosage" refers to a pharmaceutical composition of a formulation that is capable of achieving its intended effect in a single administration or application.

As used herein, "symptoms of cardiovascular disease" refers to any clinical manifestation of a disease state associated with the heart and vasculature. For example, said clinical manifestation include: angina pectoris, myocardial infarction, congestive heart failure, cardiomyopathy, hypertension, arterial stenosis, and venous stenosis. The present invention specifically contemplates treatment such that symptoms are reduced (and the condition of the subject is thereby "improved"), albeit not completely eliminated.

As used herein, "congestive heart failure" is a specific cardiovascular disease which is characterized, but not limited to, the following symptoms: shortness of breath, pitting edema, an enlarged and tender liver, engorged neck veins, and pulmonary rales in various combinations.

The terms "lower alkyl", "lower alkoxy", "lower alkanoyl", and "lower alkythio" denote such groups containing 1–8 carbon atoms, especially 2–4 carbon atoms for lower alkanoyl and 1–4 carbon atoms for the other groups. Examples of such groups include methyl, ethyl, propyl, isopropyl, n-butyl, isobutyl, tert-butyl, n-heptyl, n-octyl, methoxy, ethoxy, propoxy, n-butoxy, isobutoxy, acetyl, propionyl, butyryl, methylthio, ethylthio, propylthio and n-butylthio.

As used hereinafter, the term "active compound" denotes a pyridinone compound of general formula I (as illustrated and described below in the section entitled "Other Compounds Useful In The Treatment of Cardiovascular Disease"), or a quinolinone or quinolinone derivative as illustrated and described above.

As used herein, the term "diastereoisomers" refers to stereoisomers that are not mirror images of each other.

As used herein, the term "enantiomer" refers to stereoisomers of molecules that are non-superimposable mirror images of each other. Enantiomers have identical physical properties, such as melting points and boiling points, and also have identical spectroscopic properties. Enantiomers differ from each other with respect to their interaction with plane-polarized light and with respect to their biological activity.

As used herein, the term "stereoisomer" refers to compounds that have their atoms connected in the same order but differ in the arrangement of their atoms in space. (e.g. cis-2-butane and trans-2-butane).

As used herein, the term "racemic mixture" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

As used herein, the terms "purified enantiomer" and "purified enantiomer preparation" are meant to indicate a preparation (e.g. derived from a racemic mixture or synthesized de novo) wherein one enantiomer has been enriched over the other, and more preferably, wherein the other enantiomer represents less than 10%, and more preferably less than 5%, and still more preferably, less than 2% of the preparation.

acids or bases including inorganic acids and bases and organic acids and bases. Since the compound of the present invention is basic, salts may be prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Preferred acid addition salts are the chloride and sulfate salts.

DETAILED DESCRIPTION OF THE INVENTION

The present invention relates to methods for the treatment of cardiovascular disease. In one embodiment, the present

TABLE 1

| NONPROPRIETARY NAMES AND TRADE NAMES | CHEMICAL STRUCTURE | PREPARATIONS, USUAL DOSES, AND ROUTES OF ADMINISTRATION* |
|---|---|---|
| Amyl nitrite (isoamyl nitrite) | $H_3C\!\!-\!\!CHCH_2CH_2ONO$ / $H_3C$ | Inh: 0.18 or 0.3 ml, inhalation |
| Nitroglycerin (glyceryl trinitrate; NITRO-BID, NITROSTAT, NITROL, NITRO-DUR, others) | $H_2C-O-NO_2$<br>$HC-O-NO_2$<br>$H_2C-O-NO_2$ | T: 0.15 to 0.6 mg as needed<br>S: 0.4 mg per spray as needed<br>C: 2.5 to 9 mg two to four times daily<br>B: 1 mg every 3 to 5 h<br>O: 1.25 to 5 cm (½ to 2 in.), topically to skin every 4 to 8 h<br>D: 1 disc (2.5 to 15 mg) every 24 h<br>IV: 5 μg/min; increments of 5 μg/min |
| Isosorbide dinitrate (ISORDIL, SORBITRATE, DILATRATE, others) | (bicyclic isosorbide dinitrate structure) | T: 2.5 to 10 mg every 2 to 3 h<br>T(C): 5 to 10 mg every 2 to 3 h<br>T(O): 10 to 40 mg every 6 h<br>C: 40 to 80 mg every 8 to 12 h |
| Isosorbide-5-mononitrate (IMDUR, ISMO, others) | (bicyclic isosorbide-5-mononitrate structure) | T: 10 to 40 mg twice daily<br>C: 60 mg daily |
| Erythrityl tetranitrate (CARDILATE) | $H_2C-O-NO_2$<br>$HC-O-NO_2$<br>$HC-O-NO_2$<br>$H_2C-O-NO_2$ | T: 5 to 10 mg as needed<br>T(O): 10 mg three times daily |

B buccal (transmucosal) tablet; C, sustained-release capsule or tablet; D, transdermal disc; Inh, inhalant; IV, intravenous injection; O, ointment; S, lingual spray; T, tablet for sublingual use; T(C), chewable tablet; T(O), oral tablet or capsule.

As used herein, the phrase "pharmaceutically acceptable salts" or "a pharmaceutically acceptable salt thereof" refer to salts prepared from pharmaceutically acceptable non-toxic invention contemplates compositions and methods for the treatment of CHF and hypertension. These compositions comprise quinolinones, including derivatives and enantiomers thereof. A variety of quinolinone derivatives are shown in FIG. 1. Methods for producing antibiotic derivatives of a particular quinolone carboxylic acid skeleton are provided in U.S. Pat. No. 4,623,650 to Gilligan et al., hereby incorporated by reference.

While the present invention is not limited by the nature of the derivatives, in one embodiment, the present invention encompasses the use of a variety of quinolinone derivatives (e.g., 5-bromoquinoline, 5-nitroisoquinoline, 8-nitroisoquinoline and 1-methylisoquinoline). One skilled in the art can readily produce such derivatives as set forth in McMurry, *Organic Chemistry 2nd Ed.*, Brooks/Cole Publishing, Belmont, Calif. (1988), pages 1044–1045 and 1076.

In another embodiment, the present invention contemplates the use of methylthio and methylsulphinyl derivatives of quinolinone. In a preferred embodiment, the methylsulphinyl derivative is flosequinan (whether as a racemic mixture or as a purified enantiomer).

In another embodiment, the present invention contemplates compositions and methods for the treatment of CHF and hypertension in subjects who are not concurrently being treated with nitrites or nitrates. In a preferred embodiment, the present invention contemplates the administration of the enantiomers of flosequinan as a methods of treating CHF and hypertension. In another embodiment, the optically active derivatives and metabolites of flosequinan are also contemplated.

In one embodiment, a purified enantiomer preparation of flosequinan is administered. It is contemplated that an enantiomer of flosequinan be administered cutaneously, by standard injection, intranasally, or through respiratory inhalation. It is not intended that the methods of the present invention be limited to the mode of administration of an enantiomer of flosequinan.

A. Evaluation of Compounds for Efficacy as Anti-Hypertensives

The antihypertensive effects exerted by the enantiomers of flosequinan is readily demonstrated by means of tests on standard laboratory animals. It is not intended that the present invention be limited by the species of animal used as a test platform. Suitable animal models include, but are not limited to, species including rodents, non-human primates, ovines, bovines, ruminants, lagomorphs, porcines, caprines, equines, canines, felines, and aves.

In one embodiment, female rats (weight range 180–240 g) of the Aoki-Okamoto strain of spontaneously hypertensive can be used. The rats are divided into groups of four and will be fasted overnight before administration of either the (+) or (–) enantiomer of flosequinan. Blood pressure will be determined in the following way. The rats are placed in a restraining cage, maintained at 38° C., with their tails protruding through holes in the cage. After 30 minutes in the cage, blood pressure will be measured using an inflatable cuff placed round the base of the tail and arterial pulsations will be monitored with a pneumatic pulse transducer. In other animal models, however, a limb or a phalanx as a site to monitor blood pressure. A pressure, greater than the expected blood pressure, will be applied to the cuff and this pressure will be slowly reduced. The pressure in the cuff at which arterial pulsations reappears will be recorded as the blood pressure. The rats will be removed from the cage and each group will be orally administered a given dose of either the (+) or (–) enantiomer of flosequinan. In addition to the pre-dose reading, blood pressure will be measured at 1.5 and 5.0 hours after dosing. In one embodiment, a effective dosage will be defined as follows.

Either the (+) or (–) enantiomer of flosequinan will be tested initially at a given dose level (for example 90 mg/kg). If the compound is considered sufficiently active (giving a reduction of blood pressure equal to or greater than of approximately 15% after correction) it will be retested at a lower dose level, for example 30 mg/kg. By testing at successively lower dose levels, a threshold antihypertensive dose (dose giving a reduction of blood pressure of between 5 and 15% after correction) will be determined. Compounds which are inactive at a particular dose level and which produce a reduction of blood pressure equal to or greater than 15% after correction at the next highest dose level will be designated as having a threshold antihypertensive dose within the range covered by the two dose levels.

The above described protocol is suited it a variety of hypertensive and normotensive animal models. In a preferred embodiment, a normotensive marmoset monkey will be used.

B. Evaluation of Compounds for Efficacy in the Treatment of CHF

1. Surgical Preparation

Mature *M. fascicularis* primates will be premedicated with ketamine hydrochloride (15 mg/kg im) and glycopyrrolate (0.01 mg/kg im). Following intubation, anesthesia will be maintained with 0.5% to 1% isoflurane. A left thoracotomy, including removal of the fourth or fifth rib, will be performed under sterile conditions and the pericardium will be opened and reflected to expose the heart. Silastic catheters attached to subcutaneous vascular access ports (VAPs; Access Technology) will be inserted into the descending thoracic aorta and into the right atrium via the atrial appendage. To measure LV pressure, a solid-state micromanometer (Konigsberg Instruments) will be introduced via a stab wound in the ventricular apex and secured with a purse-string suture. A unipolar pacing lead will be sutured to the posterior wall of the LV and connected to a programmable pacemaker (Medtronic, Model Minix 8340) that will be situated subcutaneously over the left chest wall. Internal electrocardiogram (ECG) leads will be sutured to the chest wall. All catheters and wires will be tunneled subcutaneously to the dorsal midline below the scapula. Transdermal titanium skin buttons (Konigsberg Instruments) attached to the wires from the LV pressure transducer and ECG leads will be secured along the midline, while the catheter VAPs will be situated in subcutaneous pockets. The chest will be closed in layers and negative intrapleural pressure restored via a temporary chest tube. Antibiotics (Cefazolin, 30 mg/kg) will be administered subcutaneously prior to surgery and postoperatively for 10 days (30 mg/kg bid). Buprenorphine (0.01 mg/kg sq) will be administered for analgesia immediately after surgery and as needed the first postoperative week. All monkeys will be allowed to recover for a minimum of 2 weeks after surgery and were conditioned to sit in upright/reclining primate restraint chairs prior to commencement of experimental investigations.

2. Hemodynamic Measurements

Arterial blood pressure will be measured by inserting into the aortic VAP a saline-filled needle-tipped catheter, the other end of which was connected to a Statham P23 XL pressure transducer. Intravenous agents will be delivered via a similar catheter extension set inserted into the right atrial VAP. Left ventricular pressure (LVP) will be measured via the Konigsberg micromanometer and will be cross-calibrated with the aortic pressure signal, and the transthoracic ECG will be measured using a Gould ECG/Biotach amplifier (Gould Instrument Systems). All physiological signals will be sampled at 500 Hz using a computerized digital data acquisition system (Po—Ne—Mah, Gould Instrument Systems), while being simultaneously recorded on digital audio tape (Model RD 111T, Teac) and displayed on an MT 95000 eight-channel thermal-array recorder (Astro-Med). Measurements of heart rate (HR), mean arterial blood pressure (MAP), left ventricular systolic and end-diastolic blood pressures (LVSP and LVEDP, respectively), and the peak positive rate of change in LVP (+dP/dt$_{max}$) will derived using algorithm-based analyses of the digitized waveforms.

3. Myocardial Function Measurements

LV dimensions will be recorded with the primates under ketamine sedation using M-mode echocardiographic imaging (Hewlett Packard Sons 100CF) of the LV via a left transthoracic approach. Images will be recorded on VHS tape for subsequent calculation of LV fractional shortening and wall thickening percentage (WT) from the short axis and wall thickness dimensions. In addition, ejection fraction (EF) will be calculated by applying the Teicholz formula to the respective short axis dimensions measured at end-diastole and end-systole (EDV=[7/(2.4+LVDd)](LVDd$^3$) and ESV=[7/(2.4+LVD$_s$)](LVD$_s^3$) for end diastolic and end systolic volumes, respectively). Utilizing simultaneous ECG recordings on the videotape, end-diastolic dimensions will be defined as occurring at the peak of the R-wave, while end-systole will be associated with the peak of the T-wave. Systolic WT will be then calculated as the difference between end-systolic and end-diastolic dimensions and is expressed as percent change from end-diastolic thickness [(EST−EDT)/EDT]×100.

It is not intended, however, that the present invention be limited by the species of the animal model used to evaluate the efficacy of a given compound as potential CHF therapeutic. The above described protocol is suited it a variety of hypertensive and normotensive animal models. In a preferred embodiment, a normotensive marmoset monkey will be used.

The compositions utilized in the methods of the present invention comprise purified enantiomers of flosequinan, including derivatives thereof. Although the present invention is not limited by a specific means of producing enantiomers of flosequinan, methods of producing a racemic mixture of flosequinan (and methylsuphinyl/methylthio derivatives of quinolinone) are set forth in U.S. Pat. Nos. 5,079,264 and 5,011,931 to MacLean et al., hereby incorporated by reference. Moreover, a means of resolving the enantiomers of flosequinan is set forth in Morita et al., "Synthesis and Absolute Configuration of the Enantiomers of 7-Fluoro-1-methyl-3-(methylsulfinyl)-4(1H)-quinolinone (Flosequinan)," Chem. Pharm. Bull., 42(10):2157–2160 (1994), hereby incorporated by reference.

C. Resolution of the (+) and (−) Enantiomers of Flosequinan

In a preferred embodiment, the present invention contemplates the administration of a purified enantiomer of flosequinan. Many organic compounds, including flosequinan, exist in optically active forms (i.e., they have the ability to rotate the plane of plane-polarized light). In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory (rotates to the left). A compound prefixed with (+) or d is dextrorotatory (rotates to the right).

The present invention is not limited by any specific means of resolving the (+) and (−) enantiomers of flosequinan to obtain a substantially purified enantiomer of flosequinan. In one embodiment, the enantiomers were resolved according to the methods in Example 2.

It is not intended that the present invention be limited to any specific mechanism. However, the enantiomers of flosequinan can function as a vasodilator. This vasodilation decreases the total peripheral resistance offered by the vasculature, thereby, decreasing blood pressure. Flosequinan has also been reported to be a selective inhibitor of phosphodiesterase III (PDE3). (See Gristwood et al., Br. J. Pharmacol., 105:985 (1992); Frodsham et al., Eur. J. Pharmacol. 211:383 (1992)). Inhibitors of PDE3 cause vasodilation leading to a concomitant reduction in arterial blood pressure. See Shiraishi et al., Br. J. Pharmacol., 123:869–878 (1998).

It is not intended that the present invention be limited to any particular mechanism to reduce symptoms of cardiovascular disease. In one embodiment, the (+) and (−) enantiomers of flosequinan were subjected to biochemical assays to determine their respective percent inhibition of PDE3. In one embodiment, it was shown that the (+) enantiomer of flosequinan has an eight-fold increase in PDE3 inhibition as compared to that of the (−) enantiomer of flosequinan at the same molar concentration. Moreover, in the same embodiment, the (+) enantiomer of flosequinan exhibited greater inhibition of PDE3 than a racemic mixture of flosequinan at the same molar concentration. Further data concerning this is provided in Example 3.

Moreover, it is not intended that the present invention be limited to any particular mechanism to reduce the side effects associated with various pharmacological treatments for cardiovascular disease. In one embodiment, a 100 µM mixture of the (+) and (−) enantiomers of flosequinan were subjected to biochemical assays to determine their respective percent inhibition of PDE6 as compared to that of sildenafil citrate at a concentration of 1 µM. In one embodiment, it was shown that the mixture of the (+) and (−) enantiomers of flosequinan exhibited approximately half as much inhibition of PDE6 as compared to that of a 100-fold lower molar concentration of sildenafil citrate. Further data concerning this is provided in Example 1.

DIAGNOSIS OF CARDIOVASCULAR DISEASE

Determination whether an adult human is suffering from cardiovascular disease is readily made by a person skilled in the art using a number of readily available diagnostic procedures. Thus, an adult human suffering from cardiovascular disease can first be given a physical examination with particular attention to possible blood pressure or heart rhythm pathology, whereby many anatomical electophysiological cardiovascular abnormalities can be detected.

Tests to determine hypertension may be performed by doppler investigation of the venous blood return system sufficiency. Blood pressures can be determined by a number of standard techniques.

Tests to determine myocardial infarction include detecting aberrations in blood enzymes. Following a myocardial infarction the damaged heart cells release of lactate dehydrogenase (LDH) subtypes result in circulating ratios that are not normally observed in a healthy person.

Test to determine angina pectoris include testing procedures as with myocardial infarction, only with the appearance of normal LDH subtype ratios.

Test to determine congestive heart failure include comparisons of blood pressures, cardiac output and stroke volume measurement. Congestive heart failure is a debilitating progressive condition that is fatal if immediate action is not taken.

TREATMENT OF CARDIOVASCULAR DISEASE

It is not intended that the present invention be limited by the particular nature of a preparation. In one embodiment, the (+) enantiomer of flosequinan is provided together with physiologically tolerable liquid, gel or solid carriers, diluents, adjutants and excipients. In addition, enantiomers of flosequinan may be used together with other chemotherapeutic agents. On the other hand, formulations may also contain such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

The present invention is not limited by the method of introduction of the compound to the body. Among other methods, the present invention contemplates administering cutaneously, orally, or by standard injection (e.g. intravenous).

The present invention also contemplates administering the enantiomers of flosequinan to the subject intranasally or through respiratory inhalation. Formulations suitable for intranasal administration include ointments, creams, lotions, pastes, gels, sprays, aerosols, oils and other pharmaceutical carriers which accomplish direct contact between an enantiomer of flosequinan or a pharmaceutical composition comprising an enantiomer of flosequinan and the nasal cavity. Examples of pharmaceutical compositions administered intranasally are described in U.S. Pat. Nos. 5,393,773 and 5,554,639 to Craig et al.; and U.S. Pat. No. 5,801,161 to Merkus, all hereby incorporated by reference. Formulations suitable for respiratory inhalation include ointments, creams, lotions, pastes, gels, sprays, aerosols, oils and other pharmaceutical carriers which accomplish direct contact between an enantiomer of flosequinan or a pharmaceutical composition comprising an enantiomer of flosequinan and the respiratory tract. Examples of pharmaceutical compositions administered through respiratory inhalation are described in U.S. Pat. No. 4,552,891 to Hu et al.; U.S. Pat. No. 5,869,479 to Kreutner et al., and U.S. Pat. No. 5,864,037 to Chasis et al., all hereby incorporated by reference.

In some embodiments, intranasal administration and respiratory inhalation are the preferred modes of administration due to the ease of administration and faster onset of therapeutic activity. It is contemplated that intranasal administration and respiratory inhalation are advantageous as they may allow a smaller effective dosage to be administered than would be possible with the oral route of administration. A preferred mode of administration comprises administration to the lung. Intrapulmonary delivery of pharmacologic agents to subjects can be accomplished via aerosolization. Alternatively, the agent may be administered to the lung through a bronchoscope. Of course, the therapeutic agents may be investigated for their efficacy via other routes of administration, including parenteral administration.

Oral administration of an enantiomer of flosequinan is an effective mode of administration, with a mean absolute bioavailability of 72% following a single dose of fifty milligrams. Peak plasma concentrations of an enantiomer of flosequinan are observed 1–2 hours following oral administration, while peak metabolite plasma levels are observed about seven hours following oral dosage. While the present invention is not limited to a specific dosage level, for adult humans, in one preferred embodiment the dosage is a single dosage per day of 10 milligrams, while in another preferred embodiment the dosage is a single dosage per day of 25 milligrams, while in another preferred embodiment the dosage is a single dosage per day of 50 milligrams, while in yet another preferred embodiment the dosage is a single dosage per day of 75 milligrams. In another preferred embodiment, the dosage is a single dosage per day of approximately 125 milligrams and in another preferred embodiment, the dosage is a single dosage per day of approximately 150 milligrams. In another preferred embodiment, the dosage is a single dosage per day of approximately 200 milligrams. Multiple dosage is also contemplated.

Flosequinan and its enantiomers are water soluble and soluble in many organic solvents. Thus, while the present invention is not limited by the form of oral administration, aqueous and organic solution of an enantiomer of flosequinan for oral administration is contemplated. Likewise, an enantiomer of flosequinan can be associated with a solid pharmaceutical carrier for solid oral administration (i.e., in pill form). One skilled in the art is able to readily prepare such solid formulations, and in one embodiment, the inactive ingredients include croscarmellose sodium, hydroxypropyl methylcellulose, lactose, magnesium stearate, methocel E5, microcrystalline cellulose, povidine, propylene glycol and titanium dioxide.

The enantiomers of flosequinan may also be administered cutaneously in a carrier adapted for topical administration. Such carriers include creams, ointments, lotions, pastes, jellies, sprays, aerosols, bath oils, or other pharmaceutical carriers which accomplish direct contact between an enantiomer of flosequinan and the pore of the skin. In general pharmaceutical preparations may comprise from about 0.001% to about 10%, and preferably from about 0.01 to 5% by w/w of the active compound (e.g., an enantiomer of flosequinan) in a suitable carrier. In some cases it may be necessary to dissolve the active compound in an appropriate solvent such as ethanol or DMSO (dimethylsulfoxide), and the like, to facilitate incorporation into a pharmaceutical preparation.

While the present invention is not limited by a specific method of introducing an enantiomer of flosequinan by injection, injection of an enantimer of flosequinan (or a formulation comprising an enantiomer of flosequinan) can be carried out by any conventional injection means (e.g., employing an hypodermic syringe and needle or a similar device such as the NovolinPen. sold by Squibb-Novo, Inc., Princeton, N.J., USA). This injection may be by the subject injecting him or herself or by another person injecting the subject.

Flosequinan and its enantiomers can be introduced by injection in a physiologically acceptable composition. Such compositions are aqueous solutions that are physiologically acceptable for administration by injection. The physiologically acceptable carrier is selected such that it is not painful or irritating upon injection. The physiologically acceptable compositions will preferably be sterile at the time of administration by injection.

Among the physiologically acceptable compositions for use in the methods is physiological saline or phosphate buffered saline, in which the enantiomers of flosequinan are dissolved or suspended, such that the resulting composition is suitable for injection. Such a physiologically acceptable composition can also include a non-irritant preservative, such as, e.g., benzalkonium chloride at 0.05% (w/v) to 0./2% (w/v). As the skilled artisan will understand, there are numerous non-toxic salts of VIP, PHM and α-adrenergic blockers that can be employed in a physiologically acceptable composition for use in the methods herein, including, among others, the chloride, bromide, acetate, sulfate, and mesylate salts.

While the present invention is not limited to the method of injecting the enantiomers of flosequinan, in the preferred embodiment, it is injected with a standard syringe. One skilled in the art would be capable of injecting the enantiomers of flosequinan with a carrier as described above.

In view of the above, the present invention provides methods for the treatment human cardiovascular disease with the enantiomers of flosequinan (or a formulation comprising the enantiomers of flosequinan).

OTHER COMPOUNDS USEFUL IN THE TREATMENT OF CARDIOVASCULAR DISEASE

The invention is further directed to pyridinone compounds with therapeutic activity, and to compositions containing such compounds, wherein the compounds have the general formula I:

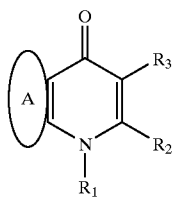

(I)

$R_1$ is hydrogen, lower alkyl optionally substituted by hydroxy or $C_{1-4}$ alkoxycarbonyl, allyl, propynyl or phenyl-lower alkyl in which the phenyl ring is optionally substituted by 1 or 2 $C_{1-4}$ alkoxy groups; $R_2$ is hydrogen or lower alkyl; $R_3$ is $(X)_m$—$S(O)_nR_4$, $COR_5$, $SR_6$, or $S(OH)(O)NR_7$, wherein m is 0 or 1, n is 0, 1, or 2, X is oxygen or lower alkylene, $R_4$ is $C_{1-4}$ alkyl, $R_5$ is hydroxyl, lower alkyl carbonyl, amino, or lower alkyl amino, and $R_6$ and $R_7$ are lower alkyl; and ring A represents an optionally substituted phenyl ring of the formula:

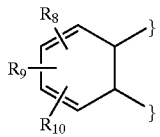

wherein $R_8$, $R_9$ and $R_{10}$, which may be the same or different, are hydrogen, lower alkyl, lower alkoxy, lower alkanoyl, halo, tri-fluoromethyl, lower alkylthio, lower alkylsulphinyl, lower alkylsulphonyl, halogenated lower alkyl, halogenated lower alkoxy, cyano, phenyl, or phenyl substituted by 1 to 3 groups independently selected from lower alkyl, lower alkoxy and trifluoromethyl; or ring A represents an optionally substituted thiophene ring of the formula:

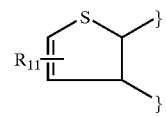

wherein $R_{11}$ is hydrogen, lower alkyl, lower alkoxy, lower alkanoyl, halo, trifluoromethyl, lower alkylthio, phenyl, or phenyl substituted by halogen, or a pharmaceutically acceptable salt thereof.

The compounds of the general formula I have been found to have antihypertensive activity and cardiac activity in warm-blooded animals. The compounds, methods of making the compounds, antihypertensive and cardiac therapeutic compositions of the compounds, and methods for treating hypertension and heart failure using the compounds are described in U.S. Pat. Nos. 4,302,460, 4,522,884, 4,855,291, 4,877,793, 4,710,506, 4,772,614 and 4,997,840, the disclosures of which patents are expressly incorporated herein, in their entirety, by reference.

In a preferred embodiment, the invention provides pharmaceutical compositions comprising compounds of the general formula I, and methods of using the compositions to treat subjects with symptoms of cardiovascular disease, such that said symptoms are reduced. As described above for the enantiomers of flosequinan, the invention is not limited by the particular nature of the pharmaceutical composition, or by the method of introduction of the active or therapeutic compound to the body. All of the treatment methods and compositions contemplated above are also contemplated here for compounds of formula I. The active ingredient in the compositions is preferably administered in unit dosage form. In one embodiment, tablets and capsules may conveniently contain a unit dosage of the active compound of 1–500 mg/kg, more preferably 5–100 mg/kg and still more preferably 5–50 mg/kg.

The compounds of formula I may contain one or more asymmetric centers and, therefore, can exist as enantiomers or diastereoisomers. Furthermore, certain compounds of formula I containing alkenyl groups may exist as cis-isomers or trans-isomers. In each case, the invention includes both mixtures and separate individual isomers. The compounds of formula I may also exist in tautomeric forms and the invention includes both mixtures and separate individual tautomers.

Preferred compounds of the general formula I for use in the pharmaceutical compositions and methods of the invention are compounds having the general formulas II and III:

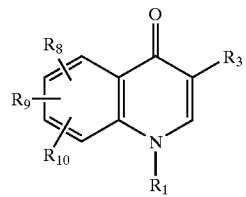

(II)

-continued

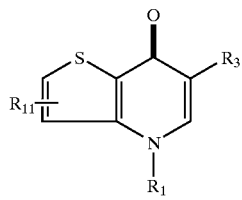
(III)

wherein $R_1$, $R_3$, $R_8$, $R_9$, $R_{10}$, and $R_{11}$ are defined as above.

With regard to compounds of formula II, still more preferred compounds have the formula IIA:

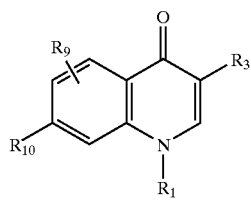
(IIA)

wherein $R_3$ is $(X)_m$—$S(O)_nR_4$, $COR_5$, $SR_6$, or $S(OH)(O)NR_7$; and (a) $R_{10}$ is hydrogen and $R_9$ is 6-lower alkoxy, 8-lower alkoxy, 5-halo or 6-halo;

(b) $R_9$ is hydrogen and $R_{10}$ is halo; lower alkyl, lower alkoxy, trifluoromethyl or lower alkyl-thio;

(c) $R_{10}$ is halo, lower alkoxy or lower alkyl and $R_9$ is 6-lower alkyl, 6-lower alkoxy or 6-halo of a different value from $R_{10}$; or (d) $R_9$ and $R_{10}$ are hydrogen.

Preferred embodiments include compounds of formula IIA wherein $R_1$ and $R_2$ are methyl, $R_9$ is hydrogen and $R_{10}$ is halo, lower alkyl or trifluoromethyl. More preferably, $R_{10}$ is halo or $C_1$–$C_4$ alkyl. In yet another preferred embodiment, $R_9$ is 6-lower alkoxy and $R_{10}$ is halo or lower alkoxy. In a further preferred embodiment, $R_9$ is 6-halo and $R_{10}$ is lower alkoxy. In another preferred embodiment, $R_{10}$ is $C_1$–$C_4$ alkyl.

Thus, preferred embodiments include compounds of formula IIB, IIC, IID, IIE, IIF, IIIA and IIIB as follows:

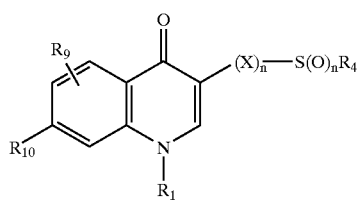
(IIB)

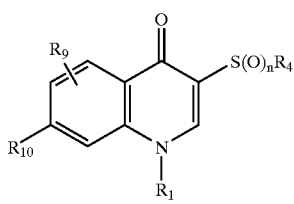
(IIC)

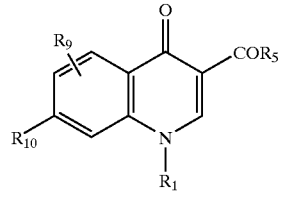
(IID)

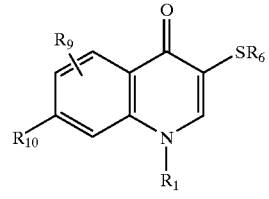
(IIE)

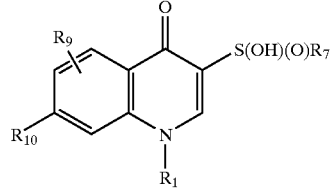
(IIF)

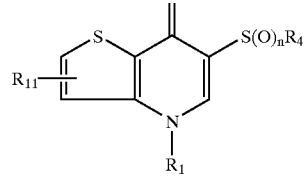
(IIIA)

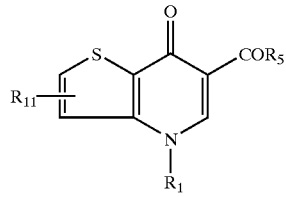
(IIIB)

Preferred compounds of formula IIB are those in which m is 1, n is 2, and X is oxygen. Preferred compounds of formula IIC include those in which m is 0, n is 1 or 2, and $R_4$ is methyl. Preferred compounds of formula IID include those in which $R_5$ is amino or lower alkyl amino. Preferred compounds of formula IIE include those in which $R_6$ is methyl. Preferred compounds of formula IIF include those in which $R_7$ is methyl. Preferred compounds of formula IIIA include those in which n is 1 and $R_4$ is methyl. Preferred compounds of formula IIIB include those in which $R_5$ is amino or lower alkyl amino.

Specific preferred compounds of these formulae include: 1-methyl-3-methylsulphinyl-4-quinolone, 7-fluoro-1-methyl-4-oxo-1,4-dihydro-quinolone-3-carboxamide, 4-methyl-7-oxo-4,7-dihydrothieno[3,2-b]pyridine-6-carboxamide, 4-methyl-6-methylsulphinyl-7(4H)-thieno[3,2-b]pyridinone, 7-chloro-1-methyl-3-methylsulphamoyl-4-quinolone, 1-methyl-4-oxo-1,4-dihydroquinol-3-yl methanesulphonate, 7-chloro-1-methyl-4-oxo-1,4-dihydroquinoline-3-carboxamide, 7-fluoro-1-methyl-3-methylsulphonyl-4-quinolone, or 7-fluoro-1-methyl-3-methylthio-4-quinolone, or pharmaceutically acceptable salts thereof.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); L (liters); ml (milliliters); µl (microliters); cm (centimeters); mm (millimeters); µm (micrometers); nm (nanometers); ° C. (nntigrade).

EXAMPLE 1

In this example, a biochemical assay was performed to test the percentage of phosphodiesterase 6 (PDE6) inhibition of various molar concentrations of sildenafil citrate (Viagra) as compared to that of a 100 µM concentration of a racemic mixture of flosequinan as follows.

PDE6 partially purified from bovine retinal rod and activated by trypsin was used. In four separate reactions, Viagra at molar concentrations of 0.3 µM, 1.0 µM, and 3.0 µM, and a 100 µM racemic mixture of flosequinan were incubated with 0.2 µg/ml active PDE6 and 100 µM cGMP containing 0.1 µM [$^3$H]cGMP in Tris buffer pH 7.5 for 20 minutes at 30° C. Each reaction was terminated by raising the temperature to 100° C. for 2 minutes. The resulting GMP was converted to guanosine by addition of 10 mg/ml snake venom nucleotidase and further incubated at 30° C. for 10 minutes. Unhydrolyzed cGMP was bound to AGI-X2 resin, and [$^3$H]guanosine remaining in the aqueous phase was quantitated by scintillation counting.

The results of the assays, as noted in the table below, indicate that although Viagra inhibits PDE6 around 50% at concentrations as low as 0.3 µM, such levels of inhibition of PDE6 require greater than 100 µM amounts of flosequinan (i.e. more than 300 times more compound on a molar basis). These empirical results could not be predicted.

| Compound | Concentration | % Inhibition of PDE6 |
| --- | --- | --- |
| Viagra | 3.0 µM | 87 |
| Viagra | 1.0 µM | 62 |
| Viagra | 0.3 µM | 57 |
| Flosequinan | 100 µM | 36 |

EXAMPLE 2

Figure 2:
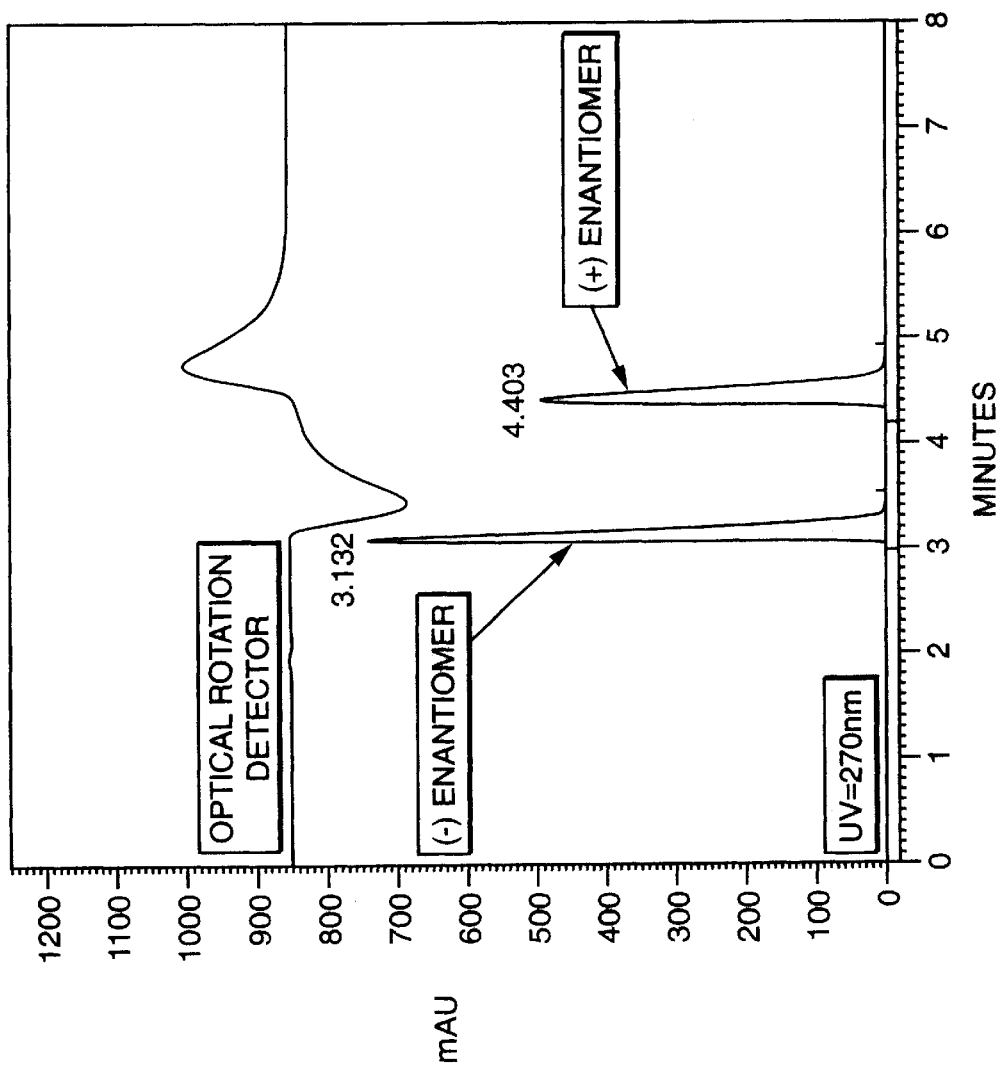
FIG. 2 depicts the respective HPLC column retention times and optical rotations of the enantiomers of flosequinan separated by the method provided in Example 2.

In this example, the enantiomers of flosequinan were resolved by high-performance liquid chromatography (HPLC) as follows. A 5.0 g sample of a racemic mixture of flosequinan was resolved over a 10 cm ID×50 cm L CHIRALCEL OD HPLC column (Chiral Technologies, Exton, Pa.) at 25° C. and with a flow rate of 1.0 ml/minute such that the column pressure was 37 bar. The mobile phase employed was 100% methanol and the detection of the mixture was performed at 270 nm. The (−) enantiomer had a retention time of 3.13 minutes, while the (+) enantiomer had a retention time of 4.40 minutes. A total of 2.1 g of the (−) enantiomer having an optical purity greater than 99% was produced. A total of 2.3 g of the (+) enantiomer having an optical purity greater than 99% was produced. (See, FIG. 2).

EXAMPLE 3

In this example, a racemic mixture of flosequinan and the (+) and (−) enantiomers of flosequinan were subjected to biochemical enzyme assays to determine their respective percent inhibition of a variety of phosphodiesterases (PDE1-PDE6). The reaction conditions for each PDE assay were as follows.

PDE1

PDE1 partially purified from bovine heart was used. A racemic mixture of flosequinan, and each enantiomer of flosequinan, all at a molar concentration of 100 µM, were independently incubated with 13 µg PDE1 enzyme, 1.0 µM [$^3$H]cAMP and CaCl$_2$/calmodulin in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE2

PDE2 partially purified from human platelets was used. A racemic mixture of flosequinan, and each enantiomer of flosequinan, all at a molar concentration of 100 µM, were independently incubated with 23 µg PDE2 enzyme, 25 µM cAMP containing 0.05 µM [$^3$H]cAMP in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE3

PDE3 partially purified from human platelets was used. A racemic mixture of flosequinan, and each enantiomer of flosequinan, all at a molar concentration of 100 µM, were independently incubated with 13 µg PDE3 enzyme and 1 µM cAMP containing 0.01 µM [$^3$H]cAMP in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE4

PDE4 partially purified from human U-937 pronocytic cells was used. A racemic mixture of flosequinan, and each enantiomer of flosequinan, all at a molar concentration of 100 µM, were independently incubated with 20 µg PDE4 enzyme and 1 µM cAMP containing 0.01 µM [$^3$H]cAMP in Tris buffer pH 7.5 for 20 minutes at 30° C. The reaction was terminated by boiling for 2 minutes, and the resulting AMP was converted to adenosine by addition of 10 mg/ml snake venom nucleotidase and further incubation at 30° C. for 10 minutes. Unhydrolyzed cAMP was bound to AGI-X2 resin, and the remaining [$^3$H]adenosine in the aqueous phase was quantitated by scintillation counting.

PDE5

PDE5 partially purified from human platelets was used. A racemic mixture of flosequinan, and each enantiomer of flosequinan, all at a molar concentration of 100 µM, were independently incubated with 120 µg PDE5 enzyme and 1 µM cGMP containing 0.01 µM [$^3$H]cGMP in Tris buffer pH 7.5 for 20 minutes at 30° C. The reaction was terminated by boiling for 2 minutes, and the resulting GMP was converted to guanosine by addition of 10 mg/ml snake venom nucleotidase and further incubation at 30° C. for 10 minutes. Unhydrolyzed cGMP was bound to AGI-X2 resin, and the remaining [³H]guanosine in the aqueous phase was quantitated by scintillation counting.

PDE6

PDE6 partially purified from bovine retinal rod and activated by trypsin was used. A racemic mixture of flosequinan, and each enantiomer of flosequinan, all at a molar concentration of 100 µM, were independently incubated with 0.2 µg/ml active PDE6 and 100 µM cGMP containing 0.1 µM [³H]cGMP in Tris buffer pH 7.5 for 20 minutes at 30° C. Each reaction was terminated by boiling for 2 minutes. The resulting GMP was converted to guanosine by addition of 10 mg/ml snake venom nucleotidase, and further incubated at 30° C. for 10 minutes. Unhydrolyzed cGMP was bound to AGI-X2 resin, and [³H]guanosine remaining in the aqueous phase was quantitated by scintillation counting.

The results of the above PDE assays are presented in the following table. The (+) enantiomer of flosequinan demonstrated more PDE1 and PDE3 inhibitory activity when compared with the (−) enantiomer of flosequinan. These empirical results could not be predicted.

| Target Phosphodiesterase | % Inhibition w/ 100 µM racemic mixture of flosequinan | % Inhibition w/ 100 µM (+)- flosequinan | % Inhibition w/ 100 µM (−)- flosequinan |
| --- | --- | --- | --- |
| PDE1 | 31 | 28 | 11 |
| PDE2 | 18 | 18 | 13 |
| PDE3 | 26 | 32 | 5 |
| PDE4 | 24 | 6 | 1 |
| PDE5 | 11 | 17 | 10 |
| PDE6 | 21 | 22 | 21 |

EXAMPLE 4

This example describes how certain preferred compounds of general formula (I) can be prepared.
 a. 7-fluoro-1-methyl-4-oxo-1,4-dihydroquinolone-3-carboxamide can be prepared as described in Example 1 of U.S. Pat. No. 4,855,291.
  (i) A mixture of ethyl 7-fluoro-4-hydroxyquinoline-3-carboxylate (4.7 g), anhydrous potassium carbonate (3.0 g), dimethyl sulphate (2.52 g) and butanone (200 ml) can be boiled under reflux for 14 hours. The solvent can be evaporated and the residue can be triturated with dichloromethane (150 ml). The mixture can be filtered and the filtrate evaporated to a small volume. Diethyl ether can be added, causing a solid to precipitate. The solid can be collected, washed with ether, dried and recrystallised from industrial methylated spirit to give the compound ethyl 7-fluoro-1-methyl-4-oxo-1,4-dihydroquinoline-3-carboxylate, m.p. 164° C.-166° C.
  (ii) A mixture of 19.0 g of the above carboxylate ester, aqueous ammonia (specific gravity 0.88, 750 ml) and caproyl alcohol (2 drops) can be stirred on a steam bath for 1.5 hours, then cooled to room temperature. The solid product can be collected by filtration and recrystallised from industrial methylated spirit/water 3:2 to give the compound 7-fluoro-1-methyl-4-oxo-1,4-dihydroquinoline3-carboxamide, m.p. 317° C.-318° C.
 b. 4-methyl-7-oxo-4,7-dihydrothieno[3,2-b]pyridine-6-carboxamide can be prepared as described in Example 1 of U.S. Pat. No. 4,877,793.
  (i) Dimethyl sulphate (3.9 ml) can be added to a stirred solution of ethyl 7-hydroxythieno[3,2-b]-pyridine-6-carboxylate (4.63 g) and potassium hydroxide (3.5 g) in water (50 ml) at 0° C.-5° C. More water (20 ml) can be added and the mixture can be stirred at ambient temperature for 24 hours. The solid product can be collected by filtration, washed with water and dried to give the compound ethyl 4-methyl-7-oxo-4,7-dihydrothieno[3,2-b]pyridine-6-carboxylate, m.p. 122° C.-128° C.
  (ii) A mixture of 3.0 g of the product from (i) above and aqueous ammonia (specific gravity 0.880, 60 ml) can be stirred and heated on a steam bath. Effervescence will occur and ocean-1-ol (2 ml) and more aqueous ammonia (specific gravity 0.880, 20 ml) can be added and heating on the steam bath can be continued overnight. The mixture can then be cooled to ambient temperature and the solid product collected by filtration, dried and crystallized from industrial methylated spirit to give the compound 4-methyl-7-oxo-4,7-dihydrothieno[3,2-b]pyridine-6-carboxamide, m.p. 255° C.-258° C.
 c. 4-methyl-6-methylsulphinyl-7(4H)-thieno[3,2-b]pyridinone can be prepared as described in Example 2 of U.S. Pat. No. 4,710,506.
  A solution of 3-chloroperbenzoic acid (85%; 1.63 g) in dichloromethane (60 ml) can be added dropwise during 20 minutes to a stirred solution of 4-methyl-6-methylthiothieno[3,2-b]pyrid-7(4H)-one (2.0 g) in dichloromethane (60 ml) at 0° C.-5° C. After 4 hours, more 3-chloroperbenzoic acid (0.15 g) in dichloromethane (10 ml) can be added and the mixture stirred overnight at ambient temperature. More 3-chloroperbenzoic acid (0.15 g) in dichloromethane (10 ml) can be added and the mixture can again be stirred overnight at ambient temperature. The resulting solution can be extracted with saturated aqueous sodium bicarbonate solution (5×150 ml) and saturated aqueous sodium chloride solution (1×150 ml) and the organic phase can be discarded. The aqueous extracts are combined and extracted with dichloromethane (5×100 ml). The organic extracts are combined, dried over anhydrous magnesium sulphate and evaporated to give a solid product. This product can be crystallized from industrial methylated spirit to give the compound 4-methyl-6-methylsulphinylthieno[3,2-b]pyrid-7(4H)-one, m.p. 174° C.-176° C.
 d. 7-chloro-1-methyl-3-methylsulphamoyl-4-quinolone can be prepared as described in Example 4 of U.S. Pat. No. 4,772,614.
  (i) 7-Chloro-1-methyl-4-quinolone (6.9 g) and chlorosulphonic acid (14 ml) can be stirred and heated at 140° C. for 2 hours. The reaction mixture can be cooled to room temperature and carefully added dropwise to ice water (200 ml). The solid which forms can be collected, washed with water and dried in air to give the compound 7-chloro-1-methyl-4-oxo-1,4-dihydroquinoline-3-sulphonyl chloride, m.p. >300° C.
  (ii) 6.5 g of the above sulphonyl chloride and aqueous methylamine (30% w/v; 220 ml) can be stirred at room temperature for 3 hours. The resulting solid can be collected, washed with water and crystallized from dichloromethane/industrial methylated spirit 1:1. The product can be collected and partitioned between water (200 ml) and dichloromethane (200 ml). The organic layer can be separated, dried over anhydrous sodium sulphate and evaporated to dryness. The residue can be crystallized from industrial methylated spirit to give the compound 7-chloro-1,N-dimethyl-4-oxo-1,4-dihydroquinoline-3-sulphonamide, m.p. 220° C.-223° C.

e. 7-chloro-1-methyl-4-oxo-1,4-dihydroquinoline-3-carboxamide can be prepared as described in Example 4 of U.S. Pat. No. 4,855,291.

A mixture of ethyl 7-chloro-1-methyl-4-oxo-1,4-dihydroquinoline-3-carboxylate (5.0 g) and aqueous ammonia (specific gravity 0.88, 100 ml) can be stirred and heated on a steam bath for 3.5 hours. More aqueous ammonia (100 ml) can be added and heating continued for a further 21 hours. The mixture can be cooled in ice. The solid product can be collected by filtration and dried to give the compound 7-chloro-1-methyl-4-oxo-1,4-dihydroquinoline-3-carboxamide, m.p. >240° C.

From the above, it should be clear that the present invention provides methods of treatment of symptoms of cardiovascular disease with pharmaceutical agents. In particular, quinolinone enantiomers are administered therapeutically to subjects having such symptoms.

We claim:

1. A method, comprising:
   a) providing:
      i) a subject exhibiting at least one symptom of cardiovascular disease, wherein said subject has not been treated in the past with a drug that causes hypotensive effects, and
      ii) a purified enantiomer preparation of flosequinan; and
   b) administering said preparation to said subject under conditions such that said symptom is reduced.

2. The method of claim 1, wherein said purified enantiomer of flosequinan is the (+) enantiomer.

3. The method of claim 1, wherein said purified enantiomer of flosequinan is the (−) enantiomer.

4. The method of claim 1, wherein said subject is an adult human and said administration comprises up to approximately 200 milligrams of said purified enantiomer of flosequinan.

5. A method, comprising:
   a) providing:
      i) a subject exhibiting at least one symptom of a cardiovascular disease selected from the group consisting of hypertension and congestive heart failure wherein said subject has not been treated in the past with a drug that causes hypotensive effects, and
      ii) a purified enantiomer preparation of flosequinan; and
   b) administering said preparation to said subject under conditions such that said symptom is reduced.

6. The method of claim 5, wherein said purified enantiomer of flosequinan is the (+) enantiomer.

7. The method of claim 5, wherein said purified enantiomer of flosequinan is the (−) enantiomer.

8. The method of claim 5, wherein said subject is an adult human and said administration comprises up to approximately 200 milligrams of said purified enantiomer of flosequinan.

* * * * *